(12) United States Patent
Wesselman et al.

(10) Patent No.: US 10,331,848 B2
(45) Date of Patent: Jun. 25, 2019

(54) METHOD FOR MANAGING COMPLEX GENOMIC DATA WORKFLOWS

(71) Applicant: ONRAMP BIOINFORMATICS, INC., San Diego, CA (US)

(72) Inventors: Timothy Wesselman, San Diego, CA (US); Jeremy Davis-Turak, San Diego, CA (US); Roshni Patel, San Diego, CA (US); Bryan Chin, San Diego, CA (US); Ali Tajeldin, San Diego, CA (US); Jean Lozach, San Diego, CA (US)

(73) Assignee: ONRAMP BIOINFORMATICS, INC., San Diego, CA (US)

( * ) Notice: Subject to any disclaimer, the term of this patent is extended or adjusted under 35 U.S.C. 154(b) by 72 days.

(21) Appl. No.: 15/715,712

(22) Filed: Sep. 26, 2017

(65) Prior Publication Data
US 2018/0218114 A1  Aug. 2, 2018

Related U.S. Application Data

(60) Provisional application No. 62/452,894, filed on Jan. 31, 2017, provisional application No. 62/452,888, filed on Jan. 31, 2017.

(51) Int. Cl.
| | | |
|---|---|---|
| G06F 16/00 | (2019.01) | |
| G06F 19/18 | (2011.01) | |
| G06F 3/06 | (2006.01) | |
| G06F 16/13 | (2019.01) | |
| G06F 16/16 | (2019.01) | |
| G06F 17/18 | (2006.01) | |

(52) U.S. Cl.
CPC ............ *G06F 19/18* (2013.01); *G06F 3/0608* (2013.01); *G06F 16/13* (2019.01); *G06F 16/162* (2019.01); *G06F 16/164* (2019.01); *G06F 17/18* (2013.01)

(58) Field of Classification Search
CPC ............................. G06F 16/164; G06F 19/18
See application file for complete search history.

*Primary Examiner* — Grace Park

(57) ABSTRACT

A method for efficiently processing and storing large data sets associated with a multi-stage bioinformatics analysis of genomic data is disclosed. The present method increases the efficiency of the electronic storage of these large data sets by automatically deleting or compressing intermediate data or a portion of output data and compressing input data, where both deletion and compression are based on predetermined characteristics of said data. When necessary, such data can be recovered using generated metadata associated with the data. Doing so, not only improves the storage efficiency of massively large genomic datasets, but also allows for the consistent reproduction of output data with the re-processing of intermediate data based on information stored in metadata.

23 Claims, 6 Drawing Sheets

| Patentable Features | Basis for Patentability | Evidence |
|---|---|---|
| (1) Deleting a first portion of the intermediate data set, wherein the first portion of the intermediate data set is designated by information stored by the set of metadata and/or by a user defined parameter | Industry teaches away. | Not one of the 11,000 open source bioinformatics applications today includes a "delete my output files" feature. The general rule in the industry is that all data is valuable and should be kept. The reasoning is, if the data is not valuable, then for what purpose was it produced? This logic holds on an individual application-basis, but breaks down when working with long, complex, multi-stage analyses. |

FIG. 3A

| Patentable Features | Basis for Patentability | Evidence (cont.) |
|---|---|---|
| (2) Generating a set of metadata associated with the experiment, the input data set, the intermediate data set, and the one or more processing applications.<br>Each set of metadata comprises<br>- data providing a name, a location, a file type, a size, or a version format of an associated intermediate data set and<br>- identifying information of the processing application and identifying information of a file storing the input data set used to produce the associated intermediate data set. | Produces surprising result of consistent results. | When the code-base of the underlying applications used in long, complex, multi-stage analyses is not frozen, any change to an included application, or its reference data (e.g., reference genomes, annotation files, etc.), will most likely result in the production of inconsistent results when compared with results produced before the change. The genomics industry, like many other emerging markets, is based on thousands of open source applications that are developed, tested, and proven in the open source community. Consequently, application updates, (and thus code changes) are the norm. |

FIG. 3B

| Patentable Features | Basis for Patentability | Evidence (cont.) |
|---|---|---|
| (2) Generating a set of metadata associated with the experiment, the input data set, the intermediate data set, and the one or more processing applications. Each set of metadata comprises<br>- data providing a name, a location, a file type, a size, or a version format of an associated intermediate data set and<br>- identifying information of the processing application and identifying information of a file storing the input data set used to produce the associated intermediate data set. | Produces surprising result of consistent results. | The standard practice in the Genomics field is to simply "re-run" any input data on the latest application and reference data to get a current result, or to simply accept that the results are inconsistent with prior analyses. While this may have been acceptable for academic institutions, this practice creates unnecessary challenges for clinical care and drug discovery/development, where consistent results have a direct impact on human lives. |

FIG. 3C

| Patentable Features | Basis for Patentability | Evidence (cont.) |
|---|---|---|
| (2) Generating a set of metadata associated with the experiment, the input data set, the intermediate data set, and the one or more processing applications. Each set of metadata comprises<br>- data providing a name, a location, a file type, a size, or a version format of an associated intermediate data set and<br>- identifying information of the processing application and identifying information of a file storing the input data set used to produce the associated intermediate data set. | Produces surprising result of consistent results. | The present invention maintains critical metadata on nearly all aspects of a particular analysis, and unconventionally stores the prior versions of applications used to produce results on the system. This combination of historical applications and the critical metadata for the analysis enables our invention to provide and ensure consistency of results now, and in the future. |

FIG. 3D

METHOD FOR MANAGING COMPLEX GENOMIC DATA WORKFLOWS

CROSS REFERENCE

This application claims priority to U.S. Patent Application No. 62/452,888, filed on Jan. 31, 2017, and U.S. Patent Application No. 62/452,894, filed on Jan. 31, 2017, the specifications of which are incorporated herein in their entirety by reference.

FIELD OF THE INVENTION

The present invention relates to a method for the management of complex genomics data requiring multi-stage analysis, interpretation, and storage.

BACKGROUND OF THE INVENTION

Bioinformatics analyses are complex, multi-stage analyses (or, alternately workflows) comprising multiple software applications. Most of the applications specific to high throughput ("HT") sequencing data have been developed in the last decade, and these are often incredibly sophisticated and intricate in their statistical and algorithmic approaches. For example, over 11,600 tools, mostly open-source, have been developed for the analysis of genomic, transcriptomic, proteomic, and metabolomic data.

One problem plaguing bioinformatics analyses is the handling of intermediate data, including temporary and log files. Such files contribute to the massive expansion of data during processing, and are often stored in obscure folders within each bioinformatics application. For example, high throughput sequencing ("HTS") experiments generate massive raw data files known as FASTQ files, which are text-based files containing nucleotide sequences and quality score information. These files are usually considered the 'raw' data. To generate useful knowledge, the raw data needs to be trimmed and cleaned, and then subjected to secondary analysis, usually including alignment to a reference genome, de novo assembly, or k-mer counting. Such analyses generate equally massive secondary and intermediate files describing the alignment, assembly, or quantification of the raw data. In turn, these derived files may often be sorted, filtered, annotated, or analyzed in any number of ways that generate even more data. All of this data, (whether stored as files, objects, or elements in a database) amount to a massive expansion (in some cases up to 5 times expansion) in the number and total footprint of the initial data, resulting in significant storage management challenges.

As another example, the amount of data generated by deep sequencing technologies is growing at an exponential rate. According to many published papers, over 40 ExaBytes ("EB") of raw genomic data are expected to be generated annually from genomic (e.g., DNA) sequencers by 2025. When taking into account the 3-5 times data expansion, this portends that an incredible 120 EB of data could be generated annually from these deep sequencing technologies.

All too often, research institutions lack a comprehensive policy and data tracking mechanism to ascertain at any time how much computer storage space is being utilized by these files. It is not uncommon for research institutions to have terabytes of HTS data scattered across hundreds of directories and folders, while the only expansion backup strategy consists of removing old hard drives and placing them on a bookshelf. Or, on the other extreme, that teams of researchers are required to meet weekly to assess which files can be deleted from overloaded data volumes. It is, therefore, paramount to incorporate data management systems and retention policies with traditional bioinformatics pipelines to track analyses and other pertinent information so that users and administrators of the system can find data, preserve analysis provenance, and enable consistent reproducibility of results.

Although genetic data may be readily available, storing, analyzing, and sharing vast quantities of genetic data can be challenging and inefficient, often obscuring significant genomic insights. For example, single-patient genetic data can become mired in a complex and unintegrated data pipeline. There is still a need in current technologies for an improved method for managing complex data workflows.

Systems and methods have been put forth to solve the aforementioned problem by tracking data individually selected for deletion and manually deleted by the user. For example, U.S. Pat. No. 8,140,814 discloses a data management apparatus and system in which a volume deletion metadata recorder records metadata for one or more volumes of data deleted by a user. After deletion, the system initiates rule-based data storage reclamation for the deleted data volumes according to a predetermined rule.

Further, U.S. Pat. No. 9,235,476 ("'476") discloses a method and system providing object versioning in a storage system that supports the logical deletion of stored objects. When a user requests the deletion of an object, the system verifies whether the deletion is prohibited and allows or denies the deletion based on the result of said verification. The utility of this logical deletion is the safeguarding of stored objects from unintentional deletion.

Currently available systems and methods, such as the above, generally do not practice deletion of data files produced by workflow stages. If deletion is practiced, it is typically carried out manually. Thus, the current technology does not address the previously discussed issue of managing the massive expansion of the initial data in complex bioinformatics workflows as users are required to identify data files ready to be deleted and must then manually carry out the deletion. Thus, the egregious task of examining the massively expanded data in order to determine which data files are ready for deletion remains. The present invention resolves this problem by automating the identification and deletion of data files. Current systems do not provide for identifying data files that are ready to be deleted and automating said deletion, on the contrary, users are still required to sift through a substantial number of data files, determine if each of said files is dispensable, and then perform the required deletions.

Moreover, deletion of intermediate data is counterintuitive to the present field of study since this data is the output of a processing stage. Therefore, some, if not all, of the intermediate data is perceived to be the highly valuable products of the data processing. It is perceived in the field that most, or all, of these files are necessary to store, especially for the verification or audit of the final data results. Thus, prior art teaches away from the objective of the present invention, which is the automatic identification and deletion of data files that are unnecessary in the processing of genomics data by a workflow.

Additionally, the present invention automatically deletes or compresses data files produced at a given stage of the bioinformatics workflow based on information, or policies, stored in metadata descriptive of the produced data file. This automated deletion or compression occurs before the next stage of the workflow begins. In this way, the expansion of initial data into the workflow is managed, thus reducing memory requirements of hardware executing the workflow. The automated deletion can occur after the completion of the workflow at a predetermined time, as defined in a data retention policy or in response to a present need to reduce storage consumption.

The prevailing thought in the present field is to maintain the latest version of the applications employed by each stage of the workflow. Results are then reproduced by reprocessing input data via the latest applications, inevitably leading to inconsistent and unreproducible results, which are required for clinical diagnostics and regulatory policies for drug development. The present invention maintains records of all parameters, application versions, and containers, via metadata files. In this way, the specific application version is referenced, via information stored in the metadata file, and accessed for accurately reprocessing input data. A significant issue in the field is producing consistent output and results, especially since the final data could include the diagnosis of a disease or confirmation of drug efficacy.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a method of automating a deletion of data generated at one or more sequential stages of a multi-stage bioinformatics analysis (i.e., workflow) of a set of genomics data. In this way, control of a potentially massive growth of total data by the multi-stage bioinformatics analysis is automated. This feature provides for a reduction in required memory repositories storing data and more efficient execution of the multi-stage bioinformatics analysis.

In some embodiments, for each sequential stage, the method comprises:
  process an input data, via one or more processing applications, to produce an intermediate data set;
  generate a set of metadata associated with the input data, the intermediate data set, and the one or more processing applications;
  store the input data, the intermediate data set, or the set of metadata in the one or more memory repositories based on one or more predetermined parameter(s), which trigger automatic storage of the input data, the intermediate data set, and the set of metadata, where the one or more predetermined parameters is based on data stored by the set of metadata or one or more user defined requirements;
  delete a portion of the intermediate data set from the memory repository storing said data set, where the first portion of the intermediate data set is designated by information stored by the set of metadata and/or by a user defined parameter; and
  pass the intermediate data set, absent the first portion of the intermediate data set, to a next stage as the input data for processing.

In an embodiment, the set of genomics data is an initial input data set processed by an initial stage of the multi-stage bioinformatics analysis. In another embodiment, the intermediate data set produced by a final stage is final data, which is stored in the one or more memory repositories. Each set of metadata generated may also be associated with the final data.

In other embodiments, after the final stage, deletion of a second portion of each intermediate data set is performed. The second portion of each intermediate data set may be designated by information stored by the set of metadata associated with each intermediate data set and/or by the user defined parameter.

In alternate embodiments, for each sequential stage, the first portion of the intermediate data set is either deleted or compressed. The first portion of the intermediate data set may be designated by information stored by the set of metadata and/or by the user defined parameter. Moreover, for each sequential stage, a first portion of the input data set may be compressed based on information stored by the set of metadata and/or by the user defined parameter. In another embodiment, after the final stage, deletion or compression of the second portion of each intermediate data set is performed. The second portion of each intermediate data set may be designated by information stored by the set of metadata associated with each intermediate data set and/or by the user defined parameter.

Additionally, the featured deletion and compression efficiently automates the management of data generated at each sequential stage of the analysis. In this way, control of a potentially massive growth of data is automated without requiring user effort, allowing for unattended processing of massive genomic datasets.

In further embodiments, the intermediate data set, absent the first portion of the intermediate data set, is optionally fully reconstituted or decompressed by identifying, via the set of metadata, the processing application and the input data set used to produce the intermediate data set. A fully reconstituted or decompressed intermediate data set may be obtained by processing the input data identified via the processing application identified and stored in the one or more memory repositories. The fully reconstituted or decompressed intermediate data set may be made available to be used as input data for further data processing, (e.g., for validating or reproducing the final data).

BRIEF DESCRIPTION OF THE DRAWINGS

The features and advantages of the present invention will become apparent from a consideration of the following detailed description presented in connection with the accompanying drawings in which:

FIG. 3A to FIG. 3D is a chart highlighting the key patentable features of the present invention.

DETAILED DESCRIPTION OF THE INVENTION

Figure 1:
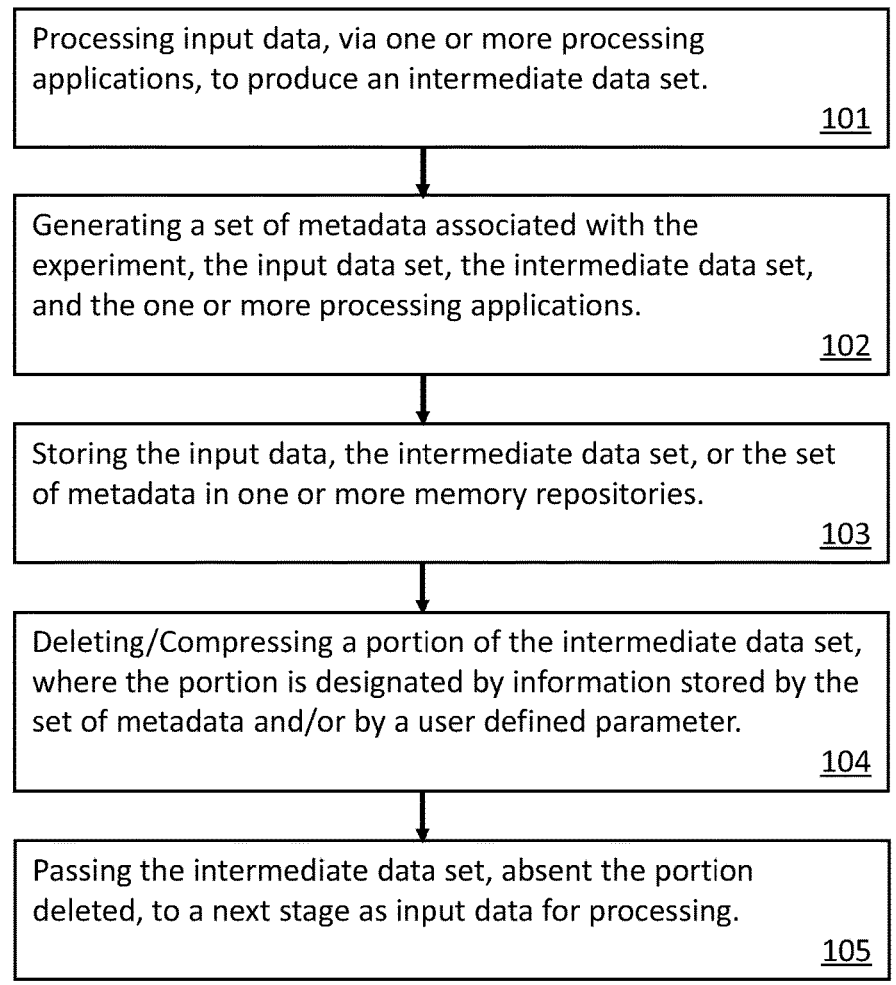
FIG. 1 is a diagram of an exemplary method of increasing efficiency in electronic storage of large data sets associated with a multi-stage bioinformatics analysis of genomic data.
Figure 2:
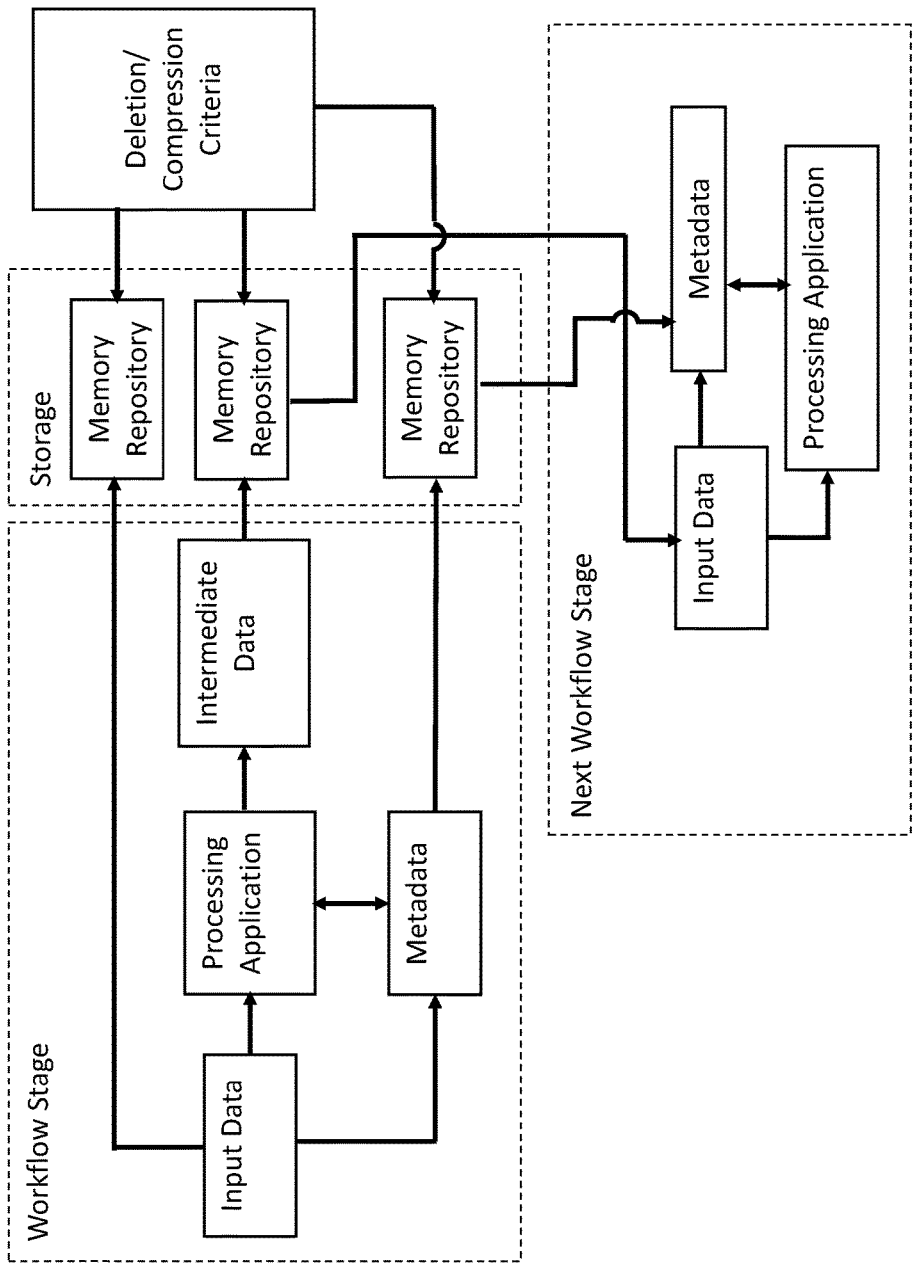
FIG. 2 is an illustration of an embodiment of the automated deletion method of a multi-stage bioinformatics analysis of genomics data. It is to be noted that the multiple memory repositories may be the same or separate repositories as will be subsequently detailed.

Referring now to FIGS. 1-3, the present invention features a method of automating a deletion of data generated at one or more sequential stages of a multi-stage bioinformatics analysis of a set of genomics data to automate control of a potentially massive growth of total data. This automated control provides for a reduction in required memory repositories storing data and a more efficient execution of said bioinformatics analysis.

In some embodiments, for each sequential stage, the method comprises:
- processing input data, via one or more processing applications, to produce an intermediate data set (101);
- generating a set of metadata associated with the bioinformatics analysis, the input data set, the intermediate data set, and the one or more processing applications (102);
- storing the experiment, the input data, the intermediate data set, or the set of metadata in one or more memory repositories (103);
- deleting a first portion of the intermediate data set, wherein the first portion of the intermediate data set is designated by information stored by the set of metadata and/or by a user defined parameter (104); and
- passing the intermediate data set, absent the first portion of the intermediate data set, to a next stage as the input data set for processing (105).

In an embodiment, the set of genomics data is an initial input data set processed by an initial stage of the multi-stage bioinformatics analysis. In another embodiment, the intermediate data set produced by a final stage is final data, which is stored in the one or more memory repositories. Each set of metadata generated may also be associated with the final data.

In other embodiments, after the final stage, deletion of a second portion of each intermediate data set is performed. The second portion of each intermediate data set may be designated by information stored by the set of metadata associated with each intermediate data set and/or by the user defined parameter.

In supplementary embodiments, each set of metadata comprises data including, but not limited to: a name, a location, a file type, a size, a version format, a species, method data generation, a disease, a condition, a group name, a control, a reference to linked files, an attribute, a value, or a set of processing parameters of an associated intermediate data set. Each set of metadata may further comprise identifying information of the processing application and of the input data used to produce the associated intermediate data set. In an embodiment, for each intermediate data set, identifying information for one or more data sets processed in earlier stages ("derivative data") is stored in the set of metadata.

In some embodiments, deletion of the portion of the intermediate data set is determined by the file type of the intermediate data set, derivative data, or the user defined parameter. The user defined parameter may be based on whether access to the intermediate data will be required at a future time.

In additional embodiments, for each sequential stage, the input data set, the intermediate data set, and the set of metadata are stored in a common memory repository. In an alternate embodiment, at least one of the input data set, the intermediate data set, or the set of metadata are stored in a memory repository separate from the common memory repository.

In further embodiments, the one or more memory repositories are tiered memory repositories, where a tier is assigned according to the memory capacity and the performance of the repository. In an embodiment, a highest tiered memory repository comprises a highest capacity memory and a highest performance (that is, relative to the other memory repositories). In other embodiments, a predetermined parameter triggers the automatic storage of the input data set and/or the intermediate data set into determined tiered memory repositories. In an embodiment, the predetermined parameter is user defined. In an alternate embodiment, the predetermined parameter comprises information stored in the set of metadata and one or more user defined requirements. In an exemplary embodiment, a tier of the repository storing the input data is lower (that is, in terms of cost and capability, relative to the other repositories) than a tier of the repository storing the intermediate data set.

In alternate embodiments, for each sequential stage, the first portion of the intermediate data set is either deleted or compressed. The first portion of the intermediate data set may be designated by information stored by the set of metadata and/or by the user defined parameter. Moreover, for each sequential stage, a first portion of the input data set may be compressed based on information stored by the set of metadata and/or by the user defined parameter. In another embodiment, after the final stage, deletion or compression of the second portion of each intermediate data set is performed. The second portion of each intermediate data set may be designated by information stored by the set of metadata associated with each intermediate data set and/or by the user defined parameter.

In further embodiments, the intermediate data set, absent the first portion of the intermediate data set, is optionally fully reconstituted or decompressed by identifying, via the set of metadata, the processing application and the input data set used to produce the intermediate data set. The fully reconstituted or decompressed intermediate data set may be obtained by processing the input data identified via the processing application identified and stored in the one or more memory repositories. The fully reconstituted or decompressed intermediate data set may be made available to be used as input data for further data processing, (e.g., for validating or reproducing the final data).

The present invention may additionally feature a system for automating a deletion of data generated at one or more sequential stages of a multi-stage bioinformatics analysis of a set of genomics data to automate control of a potentially massive growth of total data. The automated control provides for a reduction in required memory repositories storing data and more efficient execution of the multi-stage bioinformatics analysis. In some embodiments, the system comprises a processor operatively coupled to a memory storing a set of instructions for data processing and one or more processing applications. In exemplary embodiments, at least a portion of the memory comprises one or more memory repositories (e.g., disks) for storing data and RAM for storing the set of instructions for data processing.

In further embodiments, the processor executes the set of instructions, where, for each stage of the multi-stage bioinformatics analysis, said execution causes the processor to:
- process an input data, via one or more processing applications, to produce an intermediate data set;
- generate a set of metadata associated with said bioinformatics analysis, the input data, the intermediate data set, and the one or more processing applications;
- store the input data, the intermediate data set, or the set of metadata in the one or more memory repositories based on one or more predetermined parameter(s), which trigger automatic storage of the input data, the intermediate data set, and the set of metadata, where the one or more predetermined parameters is based on data stored by the set of metadata or one or more user defined requirements;
- delete a portion of the intermediate data set from the memory repository storing said data set, where the first portion of the intermediate data set is designated by information stored by the set of metadata and/or by a user defined parameter; and pass the intermediate data set, absent the first portion of the intermediate data set, to a next stage as the input data for processing.

In an embodiment, the set of genomics data is an initial input data set processed by an initial stage of the multi-stage bioinformatics analysis. In another embodiment, the intermediate data set produced by a final stage is final data, which is stored in the one or more memory repositories. Each set of metadata generated may also be associated with the final data. In an embodiment, each set of metadata comprises data including, but not limited to: a name, a location, a file type, a size, a version format, a species, method data generation, a disease, a condition, a group name, a control, a reference to linked files, an attribute, a value, or a set of processing parameters of an associated intermediate data set. Each set of metadata may further comprise identifying information of the processing application and of the input data used to produce the associated intermediate data set.

In other embodiments, after the final stage, deletion of a second portion of each intermediate data set is performed. The second portion of each intermediate data set may be designated by information stored by the set of metadata associated with each intermediate data set and/or by the user defined parameter.

In additional embodiments, for each sequential stage, the input data set, the intermediate data set, and the set of metadata are stored in a common memory repository. In an alternate embodiment, at least one of the input data set, the intermediate data set, or the set of metadata are stored in a memory repository separate from the common memory repository.

In further embodiments, the one or more memory repositories are tiered memory repositories, where a tier is assigned according to the memory capacity and the performance of the repository. In an embodiment, a highest tiered memory repository comprises a highest capacity memory and a highest performance (that is, relative to the other memory repositories). In other embodiments, a predetermined parameter triggers the automatic storage of the input data set and/or the intermediate data set into determined tiered memory repositories. In an embodiment, the predetermined parameter is user defined. In an alternate embodiment, the predetermined parameter comprises information stored in the set of metadata and one or more user defined requirements. In an exemplary embodiment, a tier of the repository storing the input data is lower than a tier of the repository storing the intermediate data set.

In alternate embodiments, for each sequential stage, the first portion of the intermediate data set is either deleted or compressed. The first portion of the intermediate data set may be designated by information stored by the set of metadata and/or by the user defined parameter. Moreover, for each sequential stage, a first portion of the input data set may be compressed based on information stored by the set of metadata and/or by the user defined parameter. In another embodiment, after the final stage, deletion or compression of the second portion of each intermediate data set is performed. The second portion of each intermediate data set may be designated by information stored by the set of metadata associated with each intermediate data set and/or by the user defined parameter.

In further embodiments, the intermediate data set, absent the first portion of the intermediate data set, is optionally fully reconstituted or decompressed by identifying, via the set of metadata, the processing application and the input data set used to produce the intermediate data set. A fully reconstituted or decompressed intermediate data set may be obtained by processing the input data identified via the processing application identified and stored in the one or more memory repositories. The fully reconstituted or decompressed intermediate data set may be made available to be used as input data for further data processing, (e.g., for validating or reproducing the final data).

Additionally, the method of the present invention may be embodied directly in hardware (as was previously detailed in the description of the system of the present invention), in a software module executed by a processor, in a combination of the two, or in a virtual machine (e.g., on a Cloud infrastructure). The software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor.

Without wishing to limit the scope or function of the present invention, following are non-limiting details of the processing applications, memory repositories, metadata, and the deletion and compression features. Further, the multi-stage analysis may alternately be referred to as a workflow and memory repositories may be alternately referred to as electronic storage spaces.

Processing Applications

The one or more processing applications may be a group of applications that are independently operable with each other. In some embodiments, different applications can process data files having the same file formats. In other embodiments, files with different formats could be used in conjunction with different applications. Moreover, it is also contemplated that different portions of a single data set could be stored using multiple file formats (e.g., txt file, doc file, xml file, gz file, FASTA format, FASTQ format, EMBL format, VCF format, etc.).

It is contemplated that the application may not be static, but rather dynamically morphing. For example, the application can be updated, revised, and/or modified by a user or others if necessary. When the application is continuously morphing, reconstruction/re-creation of data sets that were deleted may be required so that a user can track which version or stage of the application(s) generated the specific intermediate or resulting data. When reconstruction or re-creation of a data set is required, the data set can be reconstituted using associated metadata. Preferably, the metadata includes information on the application (e.g., version, commands, parameters, date, type, etc.) that was used to create the data set, and/or how and when the data set was created.

Based on the information, the deleted portion of the data set can be reconstituted by processing the input data set through the application using the parameters defined in the metadata. In this example, it is preferred that each version of the application is stored in an application container (e.g., Linux operating container) and recorded in a database (e.g., a third party data base, a Cloud database, etc.) and retrievable by using the information associated with the version of the application, thereby allowing multiple versions of a given application to be used concurrently to ensure consistency of data generation with the original parameters and application version as defined.

Memory Repositories

In some embodiments, the input data, intermediate data set, and the metadata can be stored in a single memory, or at least in a same type of storage space (e.g., split into multiple memories, etc.). In other embodiments, at least one of the input data, the intermediate data set, and the metadata can be stored in a different storage space (or in a different type of storage space) based on a preference of the user, or a predetermined parameter that triggers automatic sorting and storing of the data to different tiers of the data storage. For example, data storage spaces can be tiered into four different levels: tier 1 (high-performance, high-capacity memory (e.g., SSD or flash storage)), tier 2 (medium performance, high-capacity memory, (e.g., enterprise class hard drives)), tier 3 (low-performance, very high capacity memory, (e.g., object storage)), or tier 4 (e.g., archival tape, or glacial-class storage from cloud providers). In this example, the input data set can be stored in tier 2 data storage space after being processed through the application. The resulting (i.e., intermediate) data set while recorded in the metadata associated can be stored in tier 1 until the resulting data set or a portion of it is processed through another application. Once the analysis of the input data set and any intermediate data is completed through the entire workflow, or the next specified stage in the workflow, then the input data set can be automatically moved to the tier 3 or tier 4 storage space to allow tier 1 and/or tier 2 to have more available storage space for future projects.

Metadata

Preferably, detailed metadata is captured for every data file and data record created, modified, stored or deleted in the workflow.

It is contemplated that the one or more processing applications is operated upon as a data object, which is curated with various types of data associated with the data analysis. This includes, but is not limited to, input file(s), output file(s), log file(s), temporary file(s), and error file(s), as well as versions of each application executed against the data object and the user who authorized the action. Preferably, all such data files can be tracked by metadata associated with the data files. As used herein, metadata refers to any type of metadata, including, but not limited to: structural metadata, derivative metadata, descriptive metadata, and administrative metadata.

For example, a set of metadata associated with an input data file can include any type of metadata that provides identification, location, relationship, organization, type, and version of the data file. The metadata may also store information about a user associated with the data file. More specifically, the metadata may track:

user information comprising user ID, email address, access level, organization and job role, and/or user name,
  application ID and/or application name, application version, application parameter(s), including those used to define various ways of operating such application to govern the actions and processes exerted on input data,
  names, paths and locations of all input, output, temporary, log and error data files,
  CPU and memory resource requirements and usage by application,
  scripting commands to execute applications,
  important or relevant data points in the associated workflow stage,
  characteristics of the intermediate data including, but not limited to: quality scores, volume of data contained, summary of data results, parent, and child commands, parent and child data files, action flags, including but not limited to, archive, fork, compress, parameter values, including but not limited to cutoffs, sort criteria, comparison methods, source or original sample name and location, and output or final data file name and location.

In some embodiments, metadata engine may record, store, and track the metadata generated by each application. As used herein, metadata engine refers to a metadata tracking engine comprising an application program interface ("API") or framework for data interaction, a scalable database, a series of commands (e.g., scripts), and/or a data model. In these embodiments, it is preferred that the metadata engine capture all information including, but not limited to, files, samples, projects, experiments, commands, analyses, workflows and users.

Preferably, metadata is secured or protected such that any changes made would require authorization and prevent unauthorized modification or access. Any suitable method of securing the metadata can be used. For example, each metadata can be encrypted when it is created and decrypted when it needs to be retrieved. As another example, metadata can be stored in a storage space requiring a user password and/or user identification.

In other embodiments, metadata associated with intermediate data is used to determine when certain data files (e.g., input data files, etc.) may be deleted or moved to an alternate class of data storage independent of the last time of access or modification, as is commonly performed within the industry. Instead the determination is based on the biological objectives, project requirements, file type, the presence of derivative files, or a systematic calculation of the requirement to access the particular intermediate data file in the future. The present invention may calculate access and storage requirements for each intermediate data file to determine whether it is better stored, compressed or deleted for optional re-creation.

In an exemplary embodiment, the present invention uses metadata to calculate the optimal storage tier for the input data, the intermediate data set, and the set of final data based on the type of the processing application or on user defined requirements. Further, the present invention is able to track and inform users which processing applications are creating the largest storage costs.

Deletion

Once the input data, intermediate data set, and the metadata are stored in the electronic storage space, at least a portion of the intermediate data set (e.g., at least 30%, at least 50%, at least 70%, at least 90%) can be deleted (e.g., temporarily or permanently) from the electronic storage space. In some embodiments, input data may comprise the intermediate data set and a portion of the input data from a previous stage. In these embodiments, it is contemplated that only the intermediate data (as a whole or in part) can be deleted from the electronic data storage. However, it is also contemplated that any portion of the intermediate data set and/or input data may be deleted from the electronic data storage after the input data (a portion of the intermediate data set) is processed through the next processing application.

In a preferred embodiment, the present invention may use metadata to calculate the storage and computational costs if hosted on a cloud service provider, enabling the user to select the optimal cloud tier for genomic data based on the workflow analysis and user requirements. The present invention may also track and inform the user of which applications are creating the largest computation/storage costs. This information may be used to determine which data files to move from one cloud provider to another, or to a user memory repository according to a user-definable data policy.
Compression Once the input data, intermediate data set, and the metadata are stored in the electronic storage space, at least a portion of the intermediate data set (e.g., at least 30%, at least 50%, at least 70%, at least 90%) can be compressed (e.g., temporarily or permanently) in the electronic storage space. In some embodiments, input data may comprise the intermediate data set and a portion of the input data from a previous stage. In these embodiments, it is contemplated that only the intermediate data (as a whole or in part) can be compressed in the electronic data storage. However, it is also contemplated that any portion of the intermediate data set and/or input data may be compressed in the electronic data storage after the input data (a portion of the intermediate data set) is processed through the next processing application.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of automating a deletion of data generated at one or more sequential stages of a multi-stage bioinformatics analysis of a set of genomics data to automate control of a potentially massive growth of total data, wherein said automated control provides for a reduction in required memory repositories storing data and a more efficient execution of the multi-stage bioinformatics analysis, wherein for each sequential stage the method comprises:
   (a) processing an input data set, via one or more processing applications, to produce an intermediate data set (101);
   (b) generating a set of metadata associated with said bioinformatics analysis, the input data set, the intermediate data set, and the one or more processing applications (102);
   (c) storing the input data set, the intermediate data set, or the set of metadata in one or more memory repositories (103);
   (d) deleting a first portion of the intermediate data set, wherein the first portion of the intermediate data set is designated by information stored by the set of metadata or by a user defined parameter (104); and
   (e) passing the intermediate data set, absent the first portion of the intermediate data set, to a next stage as the input data set for processing (105), wherein the set of genomics data is an initial input data set processed by an initial stage of the multi-stage bioinformatics analysis,
   wherein the intermediate data set produced by a final stage is final data, which is stored in the one or more memory repositories,
   wherein each set of metadata generated is further associated with said final data, wherein after the final stage, deletion of a second portion of each intermediate data set is performed, wherein the second portion of each intermediate data set is designated by information stored by the set of metadata associated with each intermediate data set or by the user defined parameter.

2. The method of claim 1, wherein, for each sequential stage, the input data set, the intermediate data set, and the set of metadata are stored in a common memory repository.

3. The method of claim 2, wherein at least one of the input data set, the intermediate data set, or the set of metadata are stored in a memory repository separate from the common memory repository.

4. The method of claim 1, wherein the one or more memory repositories are tiered memory repositories, wherein a tier is assigned according to memory capacity and performance, wherein a highest tiered memory repository comprises a highest capacity memory and a highest performance.

5. The method of claim 4, wherein a predetermined parameter triggers automatic storage of the input data set or the intermediate data set into the one or more tiered memory repositories, wherein a tier of the memory repository storing the input data set is lower than a tier of the memory repository storing the intermediate data set.

6. The method of claim 5, wherein the predetermined parameter is user defined.

7. The method of claim 5, wherein the predetermined parameter comprises data stored by the set of metadata and one or more user defined requirements.

8. The method of claim 1, wherein each set of metadata comprises data providing a name, a location, a file type, a size, a version format, a species, method data generation, a disease, a condition, a group name, a control, a reference to linked files, an attribute, a value, or a set of processing parameters of an associated intermediate data set, wherein each set of metadata further comprises identifying information of the processing application and identifying information of a file storing the input data set used to produce the associated intermediate data set.

9. The method of claim 1, wherein the user defined parameter is based on whether access to the intermediate data set will be required at a future time.

10. The method of claim 1, wherein, for each sequential stage, the first portion of the intermediate data set is either deleted or compressed, wherein the first portion of the intermediate data set is designated by information stored by the set of metadata or by the user defined parameter.

11. The method of claim 1, wherein, for each sequential stage, a first portion of the input data set is compressed based on information stored by the set of metadata or by the user defined parameter.

12. The method of claim 10, wherein after the final stage, deletion or compression of the second portion of each intermediate data set is performed, wherein the second portion of each intermediate data set is designated by information stored by the set of metadata associated with each intermediate data set or by the user defined parameter.

13. The method of claim 10, wherein the intermediate data set, absent the first portion of the intermediate data set, is optionally fully reconstituted or decompressed by identifying, via the set of metadata, the processing application and the input data set used to produce the intermediate data set,
wherein a fully reconstituted or decompressed intermediate data set is obtained, by processing the input data identified via the processing application identified, and stored in the one or more memory repositories and made available to be used as input data for further data processing, wherein said further data processing comprises validating or reproducing the final data.

14. A system for automating a deletion of data generated at one or more sequential stages of a multi-stage bioinformatics analysis of a set of genomics data to automate control of a potentially massive growth of total data, wherein said automated control provides for a reduction in required memory repositories storing data and a more efficient execution of said bioinformatics analysis, wherein the system comprises:
(a) a memory storing a set of instructions and one or more processing applications, wherein at least a portion of the memory comprises one or more memory repositories; and
(b) a processor, operatively coupled to the memory, executing the set of instructions, wherein, for each stage of the multi-stage bioinformatics analysis, said execution causes the processor to:
(i) process an input data, via one or more processing applications, to produce an intermediate data set;
(ii) generate a set of metadata associated with the bioinformatics analysis, the input data, the intermediate data set, and the one or more processing applications;
(iii) store the input data, the intermediate data set, or the set of metadata in the one or more memory repositories based on a predetermined parameter, which triggers automatic storage of the input data, the intermediate data set, and the set of metadata, wherein the predetermined parameter is based on data stored by the set of metadata or one or more user defined requirements;
(iv) delete a first portion of the intermediate data set, wherein the first portion of the intermediate data set is designated by information stored by the set of metadata or by a user defined parameter; and
(v) pass the intermediate data set, absent the first portion of the intermediate data set, to a next stage as the input data for processing,
wherein the set of genomics data is an initial input data processed by an initial stage of the multi-stage bioinformatics analysis,
wherein the intermediate data set produced by a final stage is final data, which is stored in the one or more memory repositories,
wherein each set of metadata generated is further associated with said final data, wherein after the final stage, deletion of a second portion of each intermediate data set is performed, wherein the second portion of each intermediate data set is designated by information stored by the set of metadata associated with each intermediate data set or by the user defined parameter.

15. The method of claim 14, wherein, for each sequential stage, the input data, the intermediate data set, and the set of metadata are stored in a common memory repository.

16. The method of claim 15, wherein at least one of the input data, the intermediate data set, or the set of metadata are stored in a memory repository separate from the common memory repository.

17. The method of claim 14, wherein the one or more memory repositories are tiered memory repositories, wherein a tier is assigned according to memory capacity and performance, wherein a highest tiered memory repository comprises a highest capacity memory and a highest performance.

18. The method of claim 17, wherein the predetermined parameter triggers automatic storage of the input data set or the intermediate data set into the one or more tiered memory repositories, wherein a tier of the memory repository storing the input data set is lower than a tier of the memory repository storing the intermediate data set.

19. The method of claim 18, wherein the predetermined parameter is user defined.

20. The method of claim 18, wherein the predetermined parameter comprises data stored by the set of metadata and one or more user defined requirements.

21. The method of claim 14, wherein each set of metadata comprises data providing a name, a location, a file type, a size, a version format, a species, method data generation, a disease, a condition, a group name, a control, a reference to linked files, an attribute, a value, or a set of processing parameters of an associated intermediate data set, wherein each set of metadata further comprises identifying information of the processing application and identifying information of a file storing the input data set used to produce the associated intermediate data set.

22. The method of claim 14, wherein the user defined parameter is based on whether access to the intermediate data set will be required at a future time.

23. The method of claim 14, wherein the intermediate data set, absent the first portion of the intermediate data set, is optionally fully reconstituted or decompressed by identifying, via the set of metadata, the processing application and the input data used to produce the intermediate data set,
wherein a fully reconstituted or decompressed intermediate data set is obtained, by processing the input data identified via the processing application identified, and stored in the one or more memory repositories and made available to be used as input data for further data processing, wherein said further data processing comprises validating or reproducing the final data.

* * * * *